United States Patent [19]

Berg

[11] Patent Number: 5,445,716
[45] Date of Patent: * Aug. 29, 1995

[54] SEPARATION OF ETHANOL FROM ISOPROPANOL BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[*] Notice: The portion of the term of this patent subsequent to Sep. 20, 2011 has been disclaimed.

[21] Appl. No.: 323,715

[22] Filed: Oct. 18, 1994

[51] Int. Cl.⁶ .................. B01D 3/40; C07C 29/84
[52] U.S. Cl. ........................... 203/57; 203/50; 203/58; 203/59; 203/60; 203/62; 203/63; 203/64; 203/65; 203/67; 203/68; 203/69; 203/70; 568/913
[58] Field of Search ............ 203/69, 70, 62, 68, 203/63, 60, 64, 59, 58, 65, 67, 51, 57, 50; 568/913, 918

[56] References Cited

U.S. PATENT DOCUMENTS

| | | | |
|---|---|---|---|
| 2,537,115 | 1/1951 | Scheibel | 203/62 |
| 2,559,519 | 7/1951 | Smith | 203/84 |
| 2,583,412 | 1/1952 | Carlson et al. | 203/84 |
| 2,591,714 | 4/1952 | Morrell | 203/84 |
| 3,898,291 | 8/1975 | Chandrasekhara et al. | 203/99 |
| 4,710,274 | 12/1987 | Berg et al. | 203/65 |
| 5,348,625 | 9/1994 | Berg | 203/60 |

*Primary Examiner*—Wilbur Bascomb, Jr.

[57] ABSTRACT

Ethanol is difficult to separate from isopropanol by conventional distillation or rectification because of the proximity of their boiling points. Ethanol can be readily separated from isopropanol by extractive distillation. Effective agents are dipentene, anisole and ethyl benzene.

1 Claim, No Drawings

1

SEPARATION OF ETHANOL FROM ISOPROPANOL BY EXTRACTIVE DISTILLATION

FIELD OF THE INVENTION

This invention relates to a method for separating ethanol from isopropanol using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of oxygenated organic compounds, e.g. the Fischer-Tropsch process. In this mixture, a series of homologous alcohols are often produced. Two of the commonest alcohols in this mixture are ethanol and isopropanol. Ethanol boils at 78.4° C. and isopropanol at 82.4° C. The relative volatility between these two is 1.18 which makes it very difficult to separate them by conventional rectification. Extractive distillation would be an attractive method of effecting the separation of ethanol from isopropanol if agents can be found that (1) will create a large apparent relative volatility between ethanol and isopropanol and (2) are easy to recover from ethanol. Table 2 shows the relative volatility required to obtain 99% purity. With no agent, the relative volatility is 1.18 and 75 actual plates are required. With an agent giving a relative volatility of 1.6, only 27 plates are required.

OBJECTIVE OF THE INVENTION

The object of this invention is to provide a process or method of extractive distillation that will enhance the relative volatility of ethanol from isopropanol in their separation in a rectification column. It is a further object of this invention to identify organic compounds which in addition to the above constraints, are stable, can be separated from ethanol and recycled to the extractive column with little decomposition.

TABLE 2

Theoretical and Actual Plates Required vs. Relative Volatility for Ethanol - Isopropanol Separation

| Relative Volatility | Theoretical Plates Required At Total Reflux, 99% Purity | Actual Plates Required, 75% Efficiency |
|---|---|---|
| 1.18 | 56 | 75 |
| 1.3 | 35 | 47 |
| 1.5 | 23 | 31 |
| 1.6 | 20 | 27 |
| 2.2 | 13 | 18 |

SUMMARY OF THE INVENTION

The objects of this invention are to provide a process for separating ethanol from isopropanol which entails the use of certain organic compounds as the agent in extractive distillation.

TABLE 3

Effective Extractive Distillation Agents For Separating Ethanol From Isopropanol

| Compounds | Relative Volatility |
|---|---|
| None | 1.18 |
| Cumene | 1.5 |
| m-Diethyl benzene | 1.45 |
| Dicyclopentadiene | 1.35 |
| 1-Decene | 1.45 |
| 2-Heptanone | 1.3 |
| 3-Heptanone | 1.35 |
| 3-Octanone | 1.35 |
| Pinacolone | 1.4 |
| Diisobutyl ketone | 1.5 |
| Acetophenone | 1.35 |
| Propiophenone | 1.4 |
| 3-Carene | 1.3 |
| Terpinolene | 1.55 |
| Dipentene | 1.6 |
| alpha-Pinene | 1.35 |
| beta-Pinene | 1.5 |
| Limonene | 1.5 |
| alpha-Phellandrene | 1.6 |
| alpha-Terpinene | 1.6 |
| Myrcene | 1.65 |
| Carane | 1.45 |
| p-Mentha-1,5-diene | 2.2 |
| Butyl ether | 1.45 |
| 1-Methoxy-2-propanol | 1.3 |
| n-Butyl acetate | 1.4 |
| n-Amyl acetate | 1.35 |
| Ethylene glycol ethyl ether acetate | 1.3 |
| Methyl acetoacetate | 1.4 |
| Ethylene glycol diacetate | 1.3 |
| Benzyl acetate | 1.35 |
| 2-Butoxyethyl acetate | 1.35 |
| Methyl butyrate | 1.5 |
| Ethyl propionate | 1.4 |

TABLE 3-continued

Effective Extractive Distillation Agents For Separating Ethanol From Isopropanol

| Compounds | Relative Volatility |
| --- | --- |
| Ethyl n-valerate | 1.35 |
| Butyl benzoate | 1.35 |
| Ethyl benzoate | 1.3 |
| Ethyl benzene | 1.7* |
| p-Xylene | 1.45 |
| m-Xylene | 1.45 |
| o-Xylene | 1.5 |
| Octane | 1.35 |
| Pyridine | 1.3 |
| N,N-Dimethyl aniline | 1.3 |
| o-sec. Butyl phenol | 1.3 |
| 3-Isopropyl phenol | 1.3 |
| 2,6-Dimethyl phenol | 1.3 |
| o-tert. Butyl phenol | 1.35 |
| 4-Ethyl phenol | 1.35 |
| Diethyl phthalate | 1.35 |
| Diisooctyl phthalate | 1.3 |
| Dimethyl adipate | 1.3 |
| Glycerine triacetate | 1.3 |
| Decahydro naphthalene | 1.4 |
| p-Cymene | 1.5 |
| Diethyl malonate | 1.35 |
| Dimethyl glutarate | 1.35 |
| Tetrahydro furan | 1.3 |
| Diethylene glycol ethyl ether | 1.4 |
| Ethylene glycol phenyl ether | 1.3 |
| Dipropylene glycol methyl ether acetate | 1.3 |
| Dipropylene glycol methyl ether | 1.35 |
| Tripropylene glycol methyl ether | 1.3 |
| Diethylene glycol hexyl ether | 1.3 |
| Propoxypropanol | 1.5 |
| Butoxypropanol | 1.35 |
| p-Xylene glycol dimethyl ether | 1.35 |
| Propylene glycol methyl ether | 1.3 |
| Diethylene glycol t-butyl ether methyl ether | 1.35 |
| Triethylene glycol diacetate | 1.3 |
| Anisole | 1.5 |
| Phenetole | 1.5 |
| Phenyl ether | 1.35 |
| 1,2-Methylene dioxybenzene | 1.4 |
| Isophorone | 1.35 |
| Ethyl-3-ethoxypropionate | 1.4 |
| 2-Hydroxyacetophenone | 1.3 |
| Tatraethyl orthosilicate | 1.35 |
| 1,1,1-Trichloroethane | 1.35 |
| Tetrachloroethylene | 1.35 |
| 2,2,2-Trichloroethanol | 1.3 |
| m-Dichlorobenzene | 1.5 |
| Chlorobenzene | 1.35 |
| 2,6-Dichlorotoluene | 1.45 |
| 1-Chlorohexane | 1.45 |

*Data Obtained In Multiplate Rectification Column

DETAILED DESCRIPTION OF THE INVENTION

I have discovered that certain organic compounds will greatly improve the relative volatility of ethanol to isopropanol and permit the separation of ethanol from isopropanol by rectification when employed as the agent in extractive distillation. Table 3 lists the compounds that I have found to be effective. They are cumene, m-diethyl benzene, dicyclopentadiene, 1-decene, 2-heptanone, 3-heptanone, 3-octanone, pinacolone diisobutyl ketone, acetophenone, propiophenone, 3-carene, terpinolene, dipentene, alpha-pinene, beta-pinene, limonene, myrcene, alpha-phellandrene, alpha-terpinene, carane, p-mentha-1,5-diene, butyl ether, 1-methoxy-2-propanol, n-butyl acetate, n-amyl acetate, ethylene glycol ethyl ether acetate, methyl acetoacetate, ethylene glycol diacetate, benzyl acetate, 2-butoxyethyl acetate, methyl butyrate, ethyl propionate, ethyl n-valerate, butyl benzoate, ethyl benzoate, ethyl benzene, p-xylene, m-xylene, o-xylene, octane, pyridine, N,N-dimethyl aniline, o-sec. butyl phenol, 3-isopropyl phenol, 2,6-dimethyl phenol, o-tert.butyl phenol, 4-ethyl phenol, diethyl phthalate, diisooctyl phthalate, 3-carene, dimethyl adipate, glycerine triacetate, decahydro naphthalene, p-cymene, diethyl malonate, dimethyl glutarate, tetrahydro furan, diethylene glycol ethyl ether, ethylene glycol phenyl ether, dipropylene glycol methyl ether acetate, dipropylene glycol methyl ether, tripropylene glycol methyl ether, diethylene glycol hexyl ether, propoxypropanol, butoxypropanol, p-xylene glycol dimethyl ether, propylene glycol methyl ether, diethylene glycol t-butyl ether methyl ether, triethylene glycol diacetate, anisole, phenetole, phenyl ether, 1,2-methylene dioxybenzene, isophorone, ethyl-3-ethoxypropionate, 2,hydroxyacetophenone, tetraethylorthosilicate, 1,1,1-trichloroethane, tetrachloroethylene, 2,2,2-trichloroethanol, m-dichlorobenzene, chlorobenzene, 2,6-dichlorotoluene and 1-chlorohexane.

THE USEFULNESS OF THE INVENTION

The usefulness or utility of this invention can be demonstrated by referring to the data presented in Tables 1 and 2. All of the successful agents show that ethanol can be separated from isopropanol by means of extractive distillation in a rectification column and that the ease of separation as measured by relative volatility is considerable.

WORKING EXAMPLES

Example 1:

Twenty-seven grams of ethanol, 13 grams of isopropanol and 40 grams of dipentene were charged to a vapor-liquid equilibrium still and refluxed for five hours. Analysis indicated a vapor composition of 66.7% ethanol, 33.3% isopropanol; a liquid composition of 55% ethanol, 45% isopropanol. This is a relative volatility of 1.6.

Example 2:

A solution comprising 50 grams of ethanol and 50 grams of isopropanol was placed in the stillpot of a 5.6 theoretical plate glass perforated plate rectification column and heated. When refluxing began, an extractive agent consisting of ethyl benzene was pumped into the top of the column at a rate of 15 ml/min. The temperature of the extractive agent as it entered the column was 71° C. After establishing the feed rate of the extractive agent, the heat input to the ethanol and isopropanol in the stillpot was adjusted to give a total reflux rate of 40 ml/min. After 1.5 hours of operation, overhead and bottoms samples were collected and analysed by gas chromatography. The overhead composition was 78.5% ethanol, 21.5% isopropanol and the bottoms composition was 14.5% ethanol, 85.5% isopropanol. This gives a relative volatility of 1.73 for each theoretical plate.

I claim:

1. A method for recovering ethanol from a mixture of ethanol and isopropanol which comprises distilling a mixture of ethanol and isopropanol in the presence of about one part by weight of an extractive agent per part of ethanol-isopropanol mixture, recovering the ethanol as overhead product and obtaining the isopropanol and the extractive agent a bottoms product, wherein said extractive agent consists of one material selected from the group consisting of alpha-pinene, beta-pinene, limonene, alpha-phellandrene, alpha-terpinene, myrcene, carane, p-mentha-1,5-diene, butyl ether, 1-methoxy-2-propanol, n-butyl acetate, n-amyl acetate, benzyl acetate, ethylene glycol ethyl ether acetate, methyl acetoacetate, ethylene glycol diacetate, 2-butoxyethyl acetate, methyl butyrate, ethyl propionate, ethyl n-valerate, butyl benzoate, ethyl benzoate, pyridine, N,N-dimethyl aniline, o-sec.butyl phenol, 3-isopropyl phenol, 2,6-dimethyl phenol, o-tert.butyl phenol, 4-ethyl phenol, diethyl phthalate, diisooctyl phthalate, dimethyl adipate, glycerine triacetate, diethyl malonate, dimethyl glutarate, tetrahydro furan, ethylene glycol phenyl ether, dipropylene glycol methyl ether acetate, diethylene glycol hexyl ether, propoxypropanol, butoxypropanol, p-xylene glycol dimethyl ether, diethylene glycol t-butyl ether methyl ether, triethylene glycol diacetate, anisole, phenetole, phenyl ether, 1,2-methylenedioxybenzene, isophorone, ethyl-3-ethoxypropionate, tetraethylorthosilicate, 2-hydroxyacetophenone, 1,1,1-trichloroethane, tetrachloroethylene, 2,2,2-trichloroethanol, m-dichlorebenzene, chlorobenzene, 2,6-dichlorotoluene and 1-chlorohexane.

* * * * *